United States Patent
Tang et al.

(10) Patent No.: US 11,208,668 B2
(45) Date of Patent: Dec. 28, 2021

(54) NUCLEOTIDE SEQUENCE AND APPLICATION THEREOF IN ENHANCING PLANT PEST RESISTANCE

(71) Applicant: SHANGHAI JIAO TONG UNIVERSITY, Shanghai (CN)

(72) Inventors: Kexuan Tang, Shanghai (CN); Jingya Zhao, Shanghai (CN); Xueqing Fu, Shanghai (CN); Hang Liu, Shanghai (CN); Qifang Pan, Shanghai (CN); Tiantian Chen, Shanghai (CN); Hongmei Qian, Shanghai (CN); Xiaofen Sun, Shanghai (CN)

(73) Assignee: SHANGHAI JIAO TONG UNIVERSITY, Shanghai (CN)

( * ) Notice: Subject to any disclaimer, the term of this patent is extended or adjusted under 35 U.S.C. 154(b) by 0 days.

(21) Appl. No.: 16/760,447

(22) PCT Filed: Nov. 7, 2018

(86) PCT No.: PCT/CN2018/114295
§ 371 (c)(1),
(2) Date: Apr. 30, 2020

(87) PCT Pub. No.: WO2019/091390
PCT Pub. Date: May 16, 2019

(65) Prior Publication Data
US 2020/0283792 A1    Sep. 10, 2020

(30) Foreign Application Priority Data
Nov. 7, 2017 (CN) .......................... 201711082638.4

(51) Int. Cl.
*C12N 15/82* (2006.01)
*C12N 9/14* (2006.01)
*C12N 15/113* (2010.01)

(52) U.S. Cl.
CPC .......... *C12N 15/8286* (2013.01); *C12N 9/14* (2013.01); *C12N 15/113* (2013.01); *C12N 15/8205* (2013.01); *C12N 15/8216* (2013.01); *C12Y 306/01003* (2013.01); *C12N 2310/14* (2013.01)

(58) Field of Classification Search
None
See application file for complete search history.

(56) References Cited

U.S. PATENT DOCUMENTS

2003/0154517 A1*  8/2003  Allison .............. C12N 15/8205
                                                  800/284
2009/0285784 A1* 11/2009  Raemaekers ...... C12N 15/8286
                                                   424/93.2
2011/0167514 A1*  7/2011  Brover ............... C12N 15/8242
                                                  800/278

FOREIGN PATENT DOCUMENTS

CN      102206668 A    10/2011
CN      103088024 A     5/2013
CN      107937424 A     4/2018

OTHER PUBLICATIONS

Whyard et al (Insect Biochemistry and Molecular Biology 2009, 39: 824-832) (Year: 2009).*
Gen Bank AK343073 (published Jun. 2009) (Year: 2009).*
GENBANK Accession No. NM_001162178.2, May 2016.
GENBANK Accession No. CN763138.1, May 2004.
K. B. Rebijith, et al., Diet-Delivered dsRNAs for Juvenile Hormone-Binding Protein and Vacuolar ATPase-H Implied Their Potential in the Management of the Melon Aphid (Hemiptera: Aphididae), Environmental Entomology, 2016, pp. 268-275, 45(1), Oxford.
Chaobao Gao, The research of RNAi effect on the resistibility to Aphis gossypii, Agriculture, China Master's Theses Full-text Database, 2012, pp. D046-D069, No. 05.
Molecular Cloning, Cold Spring Harbor Laboratory Press, 1989, New York.

* cited by examiner

*Primary Examiner* — Stephen Uyeno
(74) *Attorney, Agent, or Firm* — Bayramoglu Law Offices LLC (57) ABSTRACT

A gene RNAi vector is constructed with a V-ATPase subunit E gene fragment, a COO2 gene fragment, or a combination of the V-ATPase subunit E gene fragment and the COO2 gene fragment, then transferred into a plant, and expressed in the plant to produce dsRNA of the V-ATPase subunit E gene, the COO2 gene, or the combination of the V-ATPase subunit E gene and the COO2 double gene, and therefore the aphid growth is suppressed, and the plant is enhanced in pest resistance.

6 Claims, 2 Drawing Sheets
Specification includes a Sequence Listing.

SEQUENCE LISTING

<160> NUMBER OF SEQ ID NOS: 10

<210> SEQ ID NO 1
<211> LENGTH: 622
<212> TYPE: DNA
<213> ORGANISM: Artificial Sequence
<220> FEATURE:
<223> OTHER INFORMATION: The sequence is a synthetized nucleotide sequence.

<400> SEQUENCE: 1

```
gtattgagtt gttggcacat aagaataaaa taaaaatttg taacacactg gaatcgcgat    60
cataactcaa caaccgtgta ttcttatttt atttttaaac attgtgtgac cttagcgcta   120
tggaactgat tgctcagcag ttggtaccag ctgtacgaac tgcattgttc ggtcgtaatc   180
accttgacta acgagtcgtc aaccatggtc gacatgcttg acgtaacaag ccagcattag   240
caaacagaaa attcgctgaa taatcgcagt aaatccctac agcaataata tgcgtattaa   300
gtttgtcttt taagcgactt attagcgtca tttagggatg tcgttattat acgcataatt   360
aaacaaaaat aaaacattct atttaaaata tttttctca ttccatttgg taactatgta    420
tttgttttta ttttgtaaga taaattttat aaaaaagagt aaggtaaacc attgatacat   480
attgcataaa ttataaccat cccatctata catagtttag gttcaataca caattatta    540
taacgtattt aatattggta gggtagatat gtatcaaatc caagttatgt gttaataaat   600
attttgagtc ttaaaactca ga                                            622
```

<210> SEQ ID NO 2
<211> LENGTH: 718
<212> TYPE: DNA
<213> ORGANISM: Artificial Sequence
<220> FEATURE:
<223> OTHER INFORMATION: The sequence is a synthetized nucleotide sequence

<400> SEQUENCE: 2

```
atgggaagtt acaaattata cgtagccgtc atggcaatag ccatagctgt agtacaggaa    60
taccttcaa tgtttaatat gcatcggcag taccgttatc ggtatcgaca tcatgtcctt    120
gttagatgcg attggtctgc cgctgaaccg tacgatgagc aggaagaagc gtctgtcgaa   180
caatctacgc taaccagacg gcgacttggc atgctactcg tccttcttcg cagacagctt   240
ttaccgatgg agcaccgtca gtgcgatgaa tacaaatcga agatctggga caaagcattt   300
aatggctacc tcgtggcagt cacgctactt atgtttagct tctagaccct gtttcgtaaa   360
agcaaccagg aggctatgca gctgatggaa ctaacgttta atacaggtaa ggaattaggc   420
tcgttggtcc tccgatacgt cgactacctt gattgcaaat tatgtccatt ccttaatccg   480
tccaacgaag tgtgctcgga cacgacgcgg gccatttta acttcatcga tgtgatggcc    540
aggttgcttc acacgagcct gtgctgcgcc cggtaaaaat tgaagtagct acactaccgg   600
accaaccaga acgcccatta ctcgctgggt atgatgaaca agatgttggc gttcatcatt   660
ggttggtctt gcgggtaatg agcgacccat actacttgtt ctacaaccgc aagtagta    718
```

<210> SEQ ID NO 3
<211> LENGTH: 1340
<212> TYPE: DNA
<213> ORGANISM: Artificial Sequence
<220> FEATURE:
<223> OTHER INFORMATION: The sequence is a synthetized nucleotide sequence

<400> SEQUENCE: 3

```
gtattgagtt gttggcacat aagaataaaa taaaaatttg taacacactg gaatcgcgat    60
cataactcaa caaccgtgta ttcttatttt atttttaaac attgtgtgac cttagcgcta   120
tggaactgat tgctcagcag ttggtaccag ctgtacgaac tgcattgttc ggtcgtaatc   180
accttgacta acgagtcgtc aaccatggtc gacatgcttg acgtaacaag ccagcattag   240
caaacagaaa attcgctgaa taatcgcagt aaatccctac agcaataata tgcgtattaa   300
gtttgtcttt taagcgactt attagcgtca tttagggatg tcgttattat acgcataatt   360
aaacaaaaat aaaacattct atttaaaata ttttttctca ttccatttgg taactatgta   420
tttgttttta ttttgtaaga taaatttat aaaaagagt aaggtaaacc attgatacat    480
attgcataaa ttataaccat cccatctata catagtttag gttcaataca caattattta   540
taacgtattt aatattggta gggtagatat gtatcaaatc caagttatgt gttaataaat   600
attttgagtc tatgggaagt tacaaattat acgtagccgt catggcaata gccatagctg   660
taaaactcag atacccttca atgtttaata tgcatcggca gtaccgttat cggtatcgac   720
tagtacagga agttagatgc gattggtctg ccgctgaacc gtacgatgag caggaagaag   780
atcatgtcct tcaatctacg ctaaccagac ggcgacttgg catgctactc gtccttcttc   840
cgtctgtcga attaccgatg gagcaccgtc agtgcgatga atacaaatcg aagatctggg   900
gcagacagct taatggctac ctcgtggcag tcacgctact tatgtttagc ttctagaccc   960
acaaagcatt tagcaaccag gaggctatgc agctgatgga actaacgttt aatacaggta  1020
tgtttcgtaa atcgttggtc ctccgatacg tcgactacct tgattgcaaa ttatgtccat  1080
aggaattagg ctccaacgaa gtgtgctcgg acacgacgcg ggccattttt aacttcatcg  1140
tccttaatcc gaggttgctt cacacgagcc tgtgctgcgc ccggtaaaaa ttgaagtagc  1200
atgtgatggc caccaaccag aacgcccatt actcgctggg tatgatgaac aagatgttgg  1260
tacactaccg gtggttggtc ttgcgggtaa tgagcgaccc atactacttg ttctacaacc  1320
cgttcatcat gcaagtagta                                              1340
```

<210> SEQ ID NO 4
<211> LENGTH: 311
<212> TYPE: DNA
<213> ORGANISM: Artificial Sequence
<220> FEATURE:
<223> OTHER INFORMATION: The sequence is a synthetized nucleotide
      sequence

<400> SEQUENCE: 4

```
gtattgagtt gttggcacat aagaataaaa taaaaatttg taacacactg gaatcgcgat    60
tggaactgat tgctcagcag ttggtaccag ctgtacgaac tgcattgttc ggtcgtaatc   120
caaacagaaa attcgctgaa taatcgcagt aaatccctac agcaataata tgcgtattaa   180
aaacaaaaat aaaacattct atttaaaata ttttttctca ttccatttgg taactatgta   240
attgcataaa ttataaccat cccatctata catagtttag gttcaataca caattattta   300
attttgagtc t                                                       311
```

<210> SEQ ID NO 5
<211> LENGTH: 359
<212> TYPE: DNA
<213> ORGANISM: Artificial Sequence
<220> FEATURE:
<223> OTHER INFORMATION: The sequence is a synthetized nucleotide
      sequence

<400> SEQUENCE: 5

```
atgggaagtt acaaattata cgtagccgtc atggcaatag ccatagctgt agtacaggaa      60
gttagatgcg attggtctgc cgctgaaccg tacgatgagc aggaagaagc gtctgtcgaa     120
ttaccgatgg agcaccgtca gtgcgatgaa tacaaatcga agatctggga caaagcattt     180
agcaaccagg aggctatgca gctgatggaa ctaacgttta atacaggtaa ggaattaggc     240
tccaacgaag tgtgctcgga cacgacgcgg gccattttta acttcatcga tgtgatggcc     300
accaaccaga acgcccatta ctcgctgggt atgatgaaca agatgttggc gttcatcat     359
```

<210> SEQ ID NO 6
<211> LENGTH: 670
<212> TYPE: DNA
<213> ORGANISM: Artificial Sequence
<220> FEATURE:
<223> OTHER INFORMATION: The sequence is a synthetized nucleotide
      sequence

<400> SEQUENCE: 6

```
gtattgagtt gttggcacat aagaataaaa taaaaatttg taacacactg gaatcgcgat      60
tggaactgat tgctcagcag ttggtaccag ctgtacgaac tgcattgttc ggtcgtaatc     120
caaacagaaa attcgctgaa taatcgcagt aaatccctac agcaataata tgcgtattaa     180
aaacaaaaat aaaacattct atttaaaata ttttttctca ttccatttgg taactatgta     240
attgcataaa ttataaccat cccatctata catagtttag gttcaataca caattattta     300
attttgagtc tatgggaagt tacaaattat acgtagccgt catggcaata gccatagctg     360
tagtacagga agttagatgc gattggtctg ccgctgaacc gtacgatgag caggaagaag     420
cgtctgtcga attaccgatg gagcaccgtc agtgcgatga atacaaatcg aagatctggg     480
acaaagcatt tagcaaccag gaggctatgc agctgatgga actaacgttt aatacaggta     540
aggaattagg ctccaacgaa gtgtgctcgg acacgacgcg ggccattttt aacttcatcg     600
atgtgatggc caccaaccag aacgcccatt actcgctggg tatgatgaac aagatgttgg     660
cgttcatcat                                                           670
```

<210> SEQ ID NO 7
<211> LENGTH: 1621
<212> TYPE: DNA
<213> ORGANISM: Artificial Sequence
<220> FEATURE:
<223> OTHER INFORMATION: The sequence is a synthetized nucleotide
      sequence

<400> SEQUENCE: 7

```
tatacccaa ccttcgtgtt tgtttcggag gggcacacca cacaccaaca gatctccccc      60
aatcatcggt cgcactcgct tcaagtacgc cgctcgttct tacccccgc ttctactctc     120
tagatcgcgt gcgtccatgc tagggcccgg tagtctactt ctgtcatgtt tgtgttagat     180
ccgtgtttgt gttagatccg tgctgctagc gttcgtacac ggatgcgacc tgtacgtcag     240
acacgttctg attgctaact tgccagtgtt tctctttggg gaatcctggg atggctctag     300
ccgttccgca gacgggatcg atttcatgat ttttttttgtt cgttgcata gggtttggtt     360
tgccctttttc ctttatttca atatatgccg tgcacttgtt tgtcgggtca tcttttcatg     420
cttttttttg tcttggttgt gatgatgtgg tctggttggg cggtcgttct agatcggagt     480
agaattaatt ctgtttcaaa ctacctggtg gatttattaa ttttggatct gtatgtgtgt     540
```

| | |
|---|---|
| gccatacata ttcatagtta cgaattgaag atgatggatg gaaatatcga tctaggatag | 600 |
| gtatacatgt tgatgcgggt tttactgatg catatacaga gatgcttttt gttcgcttgg | 660 |
| ttgtgatgat gtggtgtggt tgggcggtcg ttcattcgtt ctagatcgga gtagaatact | 720 |
| gtttcaaact acctggtgta tttattaatt ttggaactgt atgtgtgtgt catacatctt | 780 |
| catagttacg agtttaagat ggatggaaat atcgatctag gataggtata catgttgatg | 840 |
| tgggttttac tgatgcatat acatgatggc atatgcagca tctattcata tgctctaacc | 900 |
| ttgagtacct atctattata ataaacaagt atgttttata attattttga tcttgatata | 960 |
| cttggatgat ggcatatgca gcagctatat gtggattttt ttagccctgc cttcatacgc | 1020 |
| tatttatttg cttggtactg tttcttttgt cgatgctcac cctgttgttt ggtgttactt | 1080 |
| ctgcaggtcg actctagagg atccccgggt accctcgagg tcgacagatc tgctagcgt | 1140 |
| aagttactac aaacctttt gtatttatgt tccagtgaca attatttgtg ttctcatgtt | 1200 |
| ccacgtatca ctttaatgtt catggttgat cattgtaccg cctcatctct tttagaggat | 1260 |
| caagagtata tgcctgtctt aacttttct ttctctggtc cagtctttcc gctgatatta | 1320 |
| agatgaattt tacaacaaaa aatgtgctgc ctgtgtatga aggttcagag gcatagttca | 1380 |
| taatttacc ctgttctcaa ttaggaaatg tattttgcaa ggtcataaag tcttgacatt | 1440 |
| gatgatcaaa tattttctag agctaaaatt tcataatcaa atatgacagt tccacggcag | 1500 |
| tagataaaga gtacccactg tatatattag tatgaagatt aacacttgaa aaaccttg | 1560 |
| attgttccta taacacctaa tgattgacta tgacacggct gtttcgagat tttcaatcga | 1620 |
| t | 1621 |

<210> SEQ ID NO 8
<211> LENGTH: 1017
<212> TYPE: DNA
<213> ORGANISM: Artificial Sequence
<220> FEATURE:
<223> OTHER INFORMATION: The sequence is a synthetized nucleotide
      sequence

<400> SEQUENCE: 8

| | |
|---|---|
| gaattcggta ccccagcttg gtaaggaaat aattattttc tttttccctt ttagtataaa | 60 |
| atagttaagt gatgttaatt agtatgatta taataatata gttgttataa ttgtgaaaaa | 120 |
| ataatttata aatatattgt ttacataaac aacatagtaa tgtaaaaaaa tatgacaagt | 180 |
| gatgtgtaag acgaagaaga taaaagttga gagtaagtat attattttta atgaatttga | 240 |
| tcgaacatgt aagatgatat actagcatta atatttgttt taatcataat agtaattcta | 300 |
| gctggtttga tgaattaaat atcaatgata aaatactata gtaaaaataa gaataaataa | 360 |
| attaaaataa tatttttta tgattaatag tttattat aattaaatat ctataccatt | 420 |
| actaaatatt ttagtttaaa agttaataaa tattttgtta gaaattccaa tctgcttgta | 480 |
| atttatcaat aaacaaaata ttaaataaca agctaaagta acaataata tcaaactaat | 540 |
| agaaacagta atcaatgta acaaaacata atctaatgct aatataacaa agcgcaagat | 600 |
| ctatcatttt atatagtatt attttcaatc aacattctta ttaatttcta ataatactt | 660 |
| gtagttttat taacttctaa atggattgac tattaattaa atgaattagt cgaacatgaa | 720 |
| taaacaaggt aacatgatag atcatgtcat tgtgttatca ttgatcttac atttggattg | 780 |
| attacagttg ggaagctggg ttcgaaatcg ataagcttgc gctgcagtta tcatcatcat | 840 |
| catagacaca cgaaataaag taatcagatt atcagttaaa gctatgtaat atttgcgcca | 900 |

```
taaccaatca attaaaaaat agatcagttt aaagaaagat caaagctcaa aaaaataaaa        960
agagaaaagg gtcctaacca agaaaatgaa ggagaaaaac tagaaattta cctgcac         1017

<210> SEQ ID NO 9
<211> LENGTH: 24
<212> TYPE: DNA
<213> ORGANISM: Artificial Sequence
<220> FEATURE:
<223> OTHER INFORMATION: The sequence is a synthetized nucleotide
      sequence

<400> SEQUENCE: 9
atgacagttc cacggcagta gata                                               24

<210> SEQ ID NO 10
<211> LENGTH: 26
<212> TYPE: DNA
<213> ORGANISM: Artificial Sequence
<220> FEATURE:
<223> OTHER INFORMATION: The sequence is a synthetized nucleotide
      sequence

<400> SEQUENCE: 10
tttcttggtt aggacccttt tctctt                                             26
```

NUCLEOTIDE SEQUENCE AND APPLICATION THEREOF IN ENHANCING PLANT PEST RESISTANCE

CROSS REFERENCE TO THE RELATED APPLICATIONS

This application is the national phase entry of International Application No. PCT/CN2018/114295, filed on Nov. 7, 2018, which is based upon and claims priority to Chinese Patent Application No. 201711082638.4, filed on Nov. 7, 2017, the entire contents of which are incorporated herein by reference.

TECHNICAL FIELD

The present invention relates to the technical field of bioengineering, and more specifically, relates to a method for enhancing plant aphid resistance based on a dual gene fusion of V-ATPase subunit E and COO2.

BACKGROUND

Aphids are one major group of agricultural insect pests, and belong to the order Homoptera, including Adelgidae and Aphididae, ranging from 1-10 mm in body length, with piercing-sucking mouthparts. They are often clustered on leaves, terminal buds, tender stems, flower buds and other parts. There are numerous species of aphids, where approximately 4,700 species are currently known in the world, and about 1,100 species are distributed in China. When feeding, the aphids puncture the plant epidermis, parenchyma and mesophyll through the needle-like mouthparts into the sieve tube for sucking plant juices. The needle-like mouthparts can effectively avoid the defensive substances of plant epidermal tissues, which contributes to the puncturing between tissues and the smoothly sucking of nutrient-rich juices in plant tissues. Aphids suck juices from plants, which causes deterioration of nutrition, poor growth and even stagnation of the plants, resulting in reduced production. The honeydew secreted by aphids accumulates on leaves, stems and other parts, which seriously affects the photosynthesis and respiration of crops. In addition, the honeydew excreted by aphids can promote the breeding of some pathogens and the spreading of a variety of plant viruses.

The host plants of aphids include almost all families of class Coniferopsida of Angiosperms and Gymnosperms. Plant viruses can be transmitted from plant to plant by aphids, which is extremely harmful. Economic crops such as wheat, cotton, fruits, vegetables, flowers and other plants all suffer significant damage caused by aphids, resulting in huge economic losses of agriculture, forestry and horticulture. Especially in recent years, due to the influence of atmospheric greenhouse effect, the temperature is increased and a "warm winter" appears during the wheat growth period in the main wheat growing areas in China, causing serious aphid damage. The economic losses caused by aphids and their transmitted viruses are extremely serious in wheat production every year.

Since the main wheat varieties in China are all not strong in aphid resistance, how to effectively control aphids has become one of the major problems in wheat production. Pesticides play an important role in pest resistance, but pests can gradually develop resistance to pesticides, and meanwhile, the pesticides can easily cause pollution to the environment.

At present, a plant-mediated RNAi technique has emerged as one of the research focuses on pest resistance in crops, and shows a broad application prospect. This technique is realized by expressing a (double-stranded) dsRNA corresponding to an insect-specific gene in a host plant. After the insect eats the host plant, the corresponding gene is silenced and the expression level decreases, which causes the death of the insect and thus plays a role in controlling the harmful effects of pests. Therefore, the plant-mediated RNAi technique can be used to cultivate aphid-resistant varieties to achieve the purpose of safe, long-lasting and efficient control of aphids, and has important practical application value.

In sum, those skilled in the art are committed to developing a safe and effective method of aphid resistance.

SUMMARY

For the above drawbacks of the prior art, the present invention provides a safe and effective method for resisting aphids to solve the technical problems.

The first aspect of the present invention is to provide a nucleotide sequence. In a preferred embodiment, the nucleotide sequence is one selected from the following sequences:

1) a nucleotide sequence shown in any one of SEQ ID NOs: 4-6;

2) a nucleotide sequence derived from the nucleotide sequence shown in any one of SEQ ID NOs: 4-6 through substitution, deletion, insertion or addition of at least one nucleotide; and 3) a nucleotide sequence having at least 80% homology to any of SEQ ID NOs: 4-6.

The second aspect of the present invention is to provide a double-stranded RNA. In a preferred embodiment, the double-stranded RNA is composed of the above-mentioned nucleotide sequence and a reverse-complementary sequence thereof.

The third aspect of the present invention is to provide a small interfering RNA (siRNA). In a preferred embodiment, the siRNA is a short segment of double-stranded RNA molecule produced by cleavage of the above-mentioned double-stranded RNA. Preferably, the siRNA has a length of 19-25 nt.

The fourth aspect of the present invention is to provide a recombinant expression vector. In a preferred embodiment, the recombinant expression vector contains the above-mentioned nucleotide sequence or the above-mentioned double-stranded RNA molecule.

Optionally, the above-mentioned recombinant expression vector further includes a promoter capable of transcription in plants. Optionally, the promoter is a maize ubiquitin-1 promoter. The maize ubiquitin-1 promoter is located upstream of the nucleotide sequence or of the double-stranded RNA molecule. Optionally, a downstream of the maize ubiquitin-1 promoter has a rice intron (Oryza sativa rice), and the nucleotide sequence formed by fusing the maize ubiquitin-1 promoter with the rice intron (OSintron) is shown in SEQ ID NO: 7. Among them, positions 1-1080 of SEQ ID NO: 7 are the maize ubiquitin-1 promoter, wherein a nucleotide sequence in positions 1143-1621 of SEQ ID NO: 7 is the rice intron.

The fifth aspect of the present invention is to provide an application of the above-mentioned nucleotide sequence or the above-mentioned double-stranded RNA in enhancing the plant pest resistance. In a preferred embodiment, the pests are aphids.

Optionally, the aphids are one or more species selected from the group consisting of *Myzus persicae, Acyrthosiphon pisum, Diuraphis noxia, Melanaphis sacchari, Sipha flava, Aphis gossypii*, and other species.

Optionally, the plant is a dicotyledonous plant, a monocotyledonous plant, or a gymnosperm plant. Optionally, the dicotyledonous plant includes a cruciferous plant and a solanaceous plant. Optionally, the plant is one selected from the group consisting of *Arabidopsis*, rice, wheat, corn, cotton, soybean, rape, *sorghum*, tobacco, *chrysanthemum*, Chinese cabbage, cabbage, radish, and tomato.

Optionally, the application includes the following steps:

1) constructing a recombinant expression vector containing the above-mentioned nucleotide sequence or the above-mentioned double-stranded RNA molecule;

2) transforming the recombinant expression vector into *Agrobacterium*, and infecting a plant immature embryo with the *Agrobacterium*; and 3) carrying out an antibiotic screening to obtain a resistant plant seedling.

In a specific embodiment of the present invention, a method for enhancing plant aphid resistance by dual gene fusion is provided, where V-ATPase catalyzes ATP hydrolyzing to release and provide energy for various life activities, the important characteristics of the aphid salivary protein COO2 gene in the protein syntheses of aphids are used; and the advantage of the insect-resistant transgenic plants, obtained by genetic engineering, of being effective specifically against target pests without affecting non-hazardous organisms is used. Moreover, the insect-resistant substances expressed by plants exist in the plant body, and cause no pollution to the environment. Additionally, the present invention has a low cost, which is conducive to promotion.

Note: herein, each of the three sequences of SEQ ID NO: 1, SEQ ID NO: 2 and SEQ ID NO: 3 contains forward sequence parts and the complementary sequence parts; and when the three sequences of SEQ ID NO: 1, SEQ ID NO: 2 and SEQ ID NO: 3 appear herein, it should be understood as referring to the forward sequence parts thereof.

The forward sequence parts of SEQ ID NO: 1 include positions 1-60, 121-180, 241-330, 361-420, 481-540, and 601-611 (that is, the sequence shown in SEQ ID NO: 4), and their complementary sequence parts include positions 61-120, 181-240, 301-360, 421-480, 541-600, and 612-622.

The forward sequence parts of SEQ ID NO: 2 include positions 1-60, 121-180, 241-330, 361-420, 481-540, and 601-659 (that is, the sequence shown in SEQ ID NO: 5), and their complementary sequence parts includes 61-120, 181-240, 301-360, 421-480, 541-600, and 600-718.

The forward sequence parts of SEQ ID NO: 3 include positions 1-60, 121-180, 241-330, 361-420, 481-540, 601-660, 721-780, 841-900, 961-1020, 1081-1140, 1201-1260, and 1321-1330 (that is, the sequence shown in SEQ ID NO: 6), and their complementary sequence parts include positions 61-120, 181-240, 301-360, 421-480, 541-600, 661-720, 781-840, 901-960, 1021-1080, 1141-1200, 1261-1320, and 1331-1340.

The present invention is realized by the following technical solutions: the present invention relates to a aphid-resistant gene dsRNA, which is specifically formed by fusing an aphid V-ATPase subunit E gene with COO2 gene fragments, with the nucleotide sequence as shown in SEQ ID NO: 3.

The SEQ ID NO: 3 is obtained by synthesizing aphid V-ATPase subunit E gene (as shown in SEQ ID NO: 1), COO2 gene (as shown in SEQ ID NO: 2) and a fusion fragment gene of partial fragments of the V-ATPase subunit E and the COO2 genes.

The present invention relates to a method for enhancing plant aphid resistance by dual gene fusion, including: respectively constructing aphid-resistant genes by using the V-ATPase subunit E gene, the COO02 gene and a fusion fragment of partial sequences of the V-ATPase subunit E gene and the COO2 gene; constructing expression vectors and transferring the expression vectors into *Agrobacterium*, respectively; infecting wheat immature embryos with the *Agrobacterium*, and expressing dsRNAs of the V-ATPase subunit E gene, the COO2 gene, and a fusion gene formed by the V-ATPase subunit E gene and the COO2 gene in wheat respectively, so as to achieve the purpose of resisting the aphids.

The expression vectors are silencing vectors constructed with a maize ubiquitin-1 promoter to drive the V-ATPase subunit E gene, the COO2 gene and the fusion gene of the V-ATPase subunit E gene and the COO2 gene, namely RNAi vectors.

The ubiquitin-1 promoter is specifically a constitutive promoter.

The step of infecting includes: transferring the immature embryos of wheat to an *Agrobacterium* solution, then incubating on a culture medium under dark conditions to obtain immature embryogenic calli, and performing a screening of resistant regenerated plants to obtain resistant wheat seedlings.

The present invention relates to a recombinant expression vector, namely, an RNAi vector, which is constructed based on dsRNA.

The dsRNA includes:

1) a nucleotide sequence expressed in plants as shown in SEQ ID NO: 1 and a reverse-complementary sequence thereof;

2) a nucleotide sequence expressed in plants as shown in SEQ ID NO: 2 and a reverse-complementary sequence thereof, and 3) a nucleotide sequence expressed in plants as shown in SEQ ID NO: 3 and a reverse-complementary sequence thereof, wherein the nucleotide sequence as shown in SEQ ID NO: 3 consists of the nucleotide sequence as shown in SEQ ID NO: 1 and the nucleotide sequence as shown in SEQ ID NO: 2.

The aphid resistance includes:

1) an application in controlling aphids or an application in preparing a product for controlling aphids;

2) an application in promoting the death of aphids or an application in preparing a product for promoting the death of aphids; and 3) an application in suppressing the growth of aphids or an application in preparing a product for suppressing the growth of aphids.

Technical Effects

The experiments of the present disclosure prove that the dsRNAs of the aphid V-ATPase subunit E gene, the COO2 gene, and the fusion fragment of the V-ATPase subunit E gene and the COO2 gene expressed corresponding complementary DNA (cDNA) sequences in wheat, result in the lethal effect of wheat aphids. Among them, the dsRNA of the fusion fragment of the V-ATPase subunit E gene and the COO2 gene that expressing the cDNA sequence thereof has the best resistant effect on aphids.

Compared with chemical control, the insect-resistant transgenic plants obtained by genetic engineering have the advantage of being effective specifically against target pests without affecting non-hazardous organisms. Moreover, the insect-resistant substances expressed by plants exist in the plant body, and cause no pollution to the environment. Additionally, the present invention has a low cost, which is conducive to promotion.

Compared with the prior art, the present invention has no particular limitation on plants applicable to the present invention. The plants are suitable for gene transformation operations, such as various crops, flower plants, and forestry plants.

BRIEF DESCRIPTION OF THE DRAWINGS

FIGS. 1a, 1b and 1c are schematic diagrams showing the construction of pDE1005: proUBI: V-ATPase subunit E+COO2 vector in the present invention; wherein, FIG. 1a is a schematic diagram of the pDE1005 vector.

in this figure: M represents Marker III; + represents the pDE1005: proUBI: V-ATPase subunit E+COO2 plasmid; CK represents a wild-type Fileder spring wheat; 1-1, 1-3, 1-6, 2-3, 2-3, 2-6, 3-2, 3-4, 3-6, 4-1, 4-3, 4-4, 5-3, 5-5, and 5-8 represent transgenic T1 generation wheat plants with V-ATPase subunit E gene+COO2 gene driven by ubiquitin-1 promoter, referred to as VC.

in this figure: M represents Marker III; + represents the pDE1005: proUBI: V-ATPase subunit E+COO2 plasmid; CK represents a wild-type Fileder spring wheat; 1-1, 1-3, 1-6, 2-3, 2-3, 2-6, 3-2, 3-4, 3-6, 4-1, 4-3, 4-4, 5-3, 5-5, and 5-8 represent transgenic TI generation wheat plants with V-ATPase subunit E gene+COO2 gene driven by ubiquitin-1 promoter, referred to as VC.

DETAILED DESCRIPTION OF THE EMBODIMENTS

The experimental methods in the following embodiments without specifying specific conditions are generally conducted under conventional conditions, such as the conditions according to Molecular Cloning: A Laboratory Manual (New York: Cold Spring Harbor Laboratory Press, 1989) by Joe Sambrook et al, or as recommended by manufacturers. Unless otherwise specified, the reagents used are all commercially available or publicly available.

During the growth and development of aphids, V-ATPase catalyzes ATP hydrolyzing to release and provide energy for various life activities, and the salivary protein COO2 gene also plays an important role in the protein syntheses of aphids. Therefore, in a specific embodiment of the present invention, fragments of the V-ATPase and COO2 genes are used for gene fusion to construct an element for gene silencing, through which the expression levels of the V-ATPase and COO2 genes in aphids are reduced and thus the normal growth and development of aphids are affected, thereby achieving the purpose of suppressing the growth of aphids.

In a specific embodiment, fragments of non-conserved regions of V-ATPase subunit E and COO2 genes are fused to construct an element for gene silencing. The non-conserved regions are selected for preventing the interference of other homologous sequences except the aphid V-ATPase subunit E and COO2 sequences.

In a specific embodiment, the element used for gene silencing is a double-stranded RNA.

In a specific embodiment, the fragments of the non-conserved regions of the aphid V-ATPase subunit E and COO2 genes are fused, and a recombinant expression vector containing the forward and reverse sequences of the fusion gene is constructed. The recombinant expression vector is transferred into a plant (e.g., by *Agrobacterium*-mediated infection), and then the dsRNA of the fusion gene formed by the V-ATPase subunit E and COO2 genes is expressed in the plants. After eating the transgenic plants producing both siRNAs of the V-ATP and COO2 genes, the expression levels of both the V-ATPase subunit E and COO2 genes in the aphids decreased simultaneously. The above-mentioned RNA interference affects the normal growth and development of aphids, so as to achieve the purpose of suppressing the growth of aphids.

"RNA interference (RNAi)" refers to a process in which some small double-stranded RNAs can efficiently and specifically block the expression of specific target genes in vivo, promote the degradation of mature mRNA, and thus cause biological individuals to exhibit the phenotype of specific gene deletion. RNA interference causes a highly specific gene silencing or suppression at the mRNA level.

"Small interfering RNA (siRNA)" refers to a short double-stranded RNA molecule that can degrade specific mRNA by targeting the mRNA with homologous complementary sequences, and this process is the RNA interference pathway.

By comparing the sequences of the V-ATPase subunit E and COO2 genes that have been sequenced in various species of aphids, it can be seen that these two gene sequences are extremely conservative. Although these two gene sequences in the aphids from other dicotyledonous and monocotyledonous plants have not been sequenced, it can be speculated that these two genes have extremely high homology in different species of aphids. If the RNAi can be realized in wheat, it can be realized in other plants (such as monocotyledons, dicotyledons, gymnosperms) as well.

Embodiment 1 Sequence Alignment of V-ATPase Subunit E and COO2 Genes for Homology Identification Using the NCBI database, the selected V-ATPase subunit E gene fragment (SEQ ID NO: 4) was subjected to nucleic acid sequence alignment. The results show that this sequence is 100% homologous to the V-type proton ATPase subunit E-like sequence of *Acyrthosiphon pisum* (NCBI accession number: XM_001162178.2), 95% homologous to the V-type proton ATPase subunit E-like sequence of *Myzus persicae* (NCBI accession number: XM_022312248.1), 92% homologous to the V-type proton ATPase subunit E-like sequence of *Diuraphis noxia* (NCBI accession number: XM_015522279.1), 94% homologous to the V-type proton ATPase subunit E-like sequence of *Melanaphis sacchari* (NCBI accession number: XM_025342771.1), and 86% homologous to the V-type proton ATPase subunit E-like sequence of *Sipha flava* (NCBI accession number: XM_025565024.1).

The selected COO02 gene fragment (SEQ ID NO: 5) was subjected to nucleic acid sequence alignment. The results show that this sequence is 99% homologous to the sequence of *Acyrthosiphon pisum* (NCBI accession number: XM_001948323.3), 89%0 homologous to the sequence of *Myzus persicae* (NCBI accession number: XM_022310905.1), 89% homologous to the sequence of *Aphis gossypii* (NCBI accession number: KJ451424.1), and 80% homologous to the sequence of *Melanaphis sacchari* (NCBI accession number: XM_025338353.1).

According to the principle of the RNAi technique, gene sequences with more than 80%⁰ homology to the V-ATPase subunit E and COO2 gene sequences of the present invention have resistance to aphids.

Figure 1A:
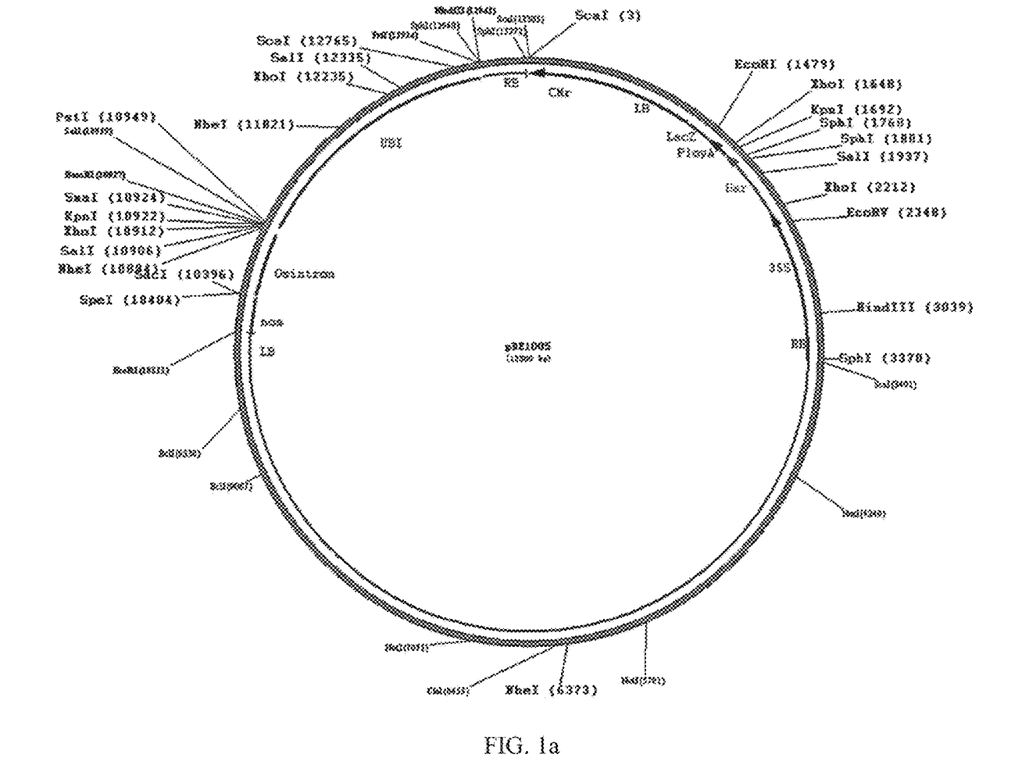
Figure 1B:
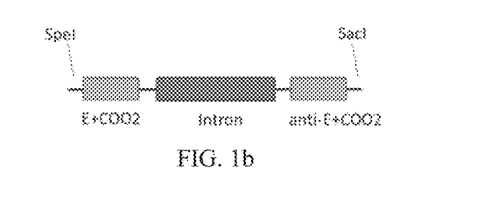
FIG. 1b is a schematic diagram of the construction of a V-ATPase subunit E+COO2 hairpin structure.
Figure 1C:
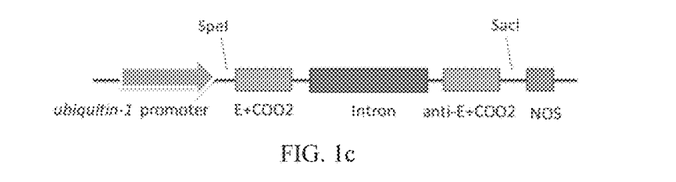
FIG. 1c is a schematic diagram showing a partial structure of the vector after being connected with the hairpin structure of FIG. 1b.
Figure 2:
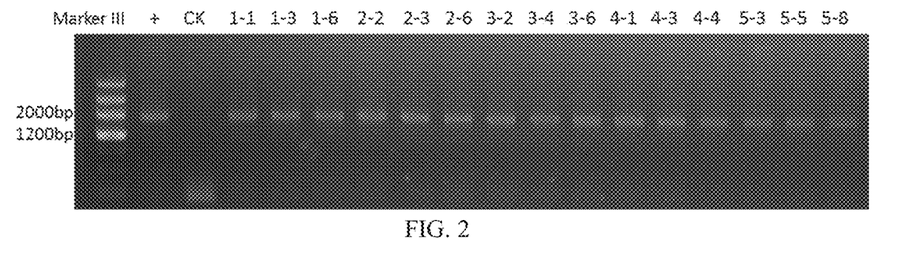
FIG. 2 is a schematic diagram of PCR identification of transgenic TI generation wheat with V-ATPase subunit E gene+COO2 gene driven by ubiquitin-1 promoter in the embodiment.
Figure 3:
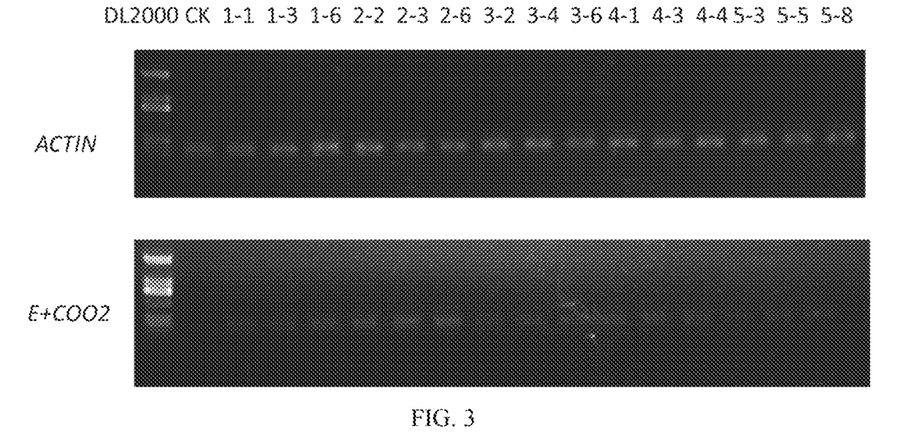
FIG. 3 is a schematic diagram showing semi-quantitative results of V-ATPase subunit E+COO2 gene of transgenic TI-generation wheat with V-ATPase subunit E gene+COO2 gene driven by ubiquitin-1 promoter in the embodiment.

Embodiment 2 Synthesis of RNAi Vector Containing V-ATPase Subunit E Gene and COO2 Gene A V-ATPase subunit E gene fragment, a COO02 gene fragment, and a fusion gene fragment formed by the V-ATPase subunit E gene and COO02 gene were synthesized to separately construct a hairpin structure containing a forward gene, an intron sequence, and a reverse gene, and then the hairpin structures were constructed into the pDE1005 vector (purchased from Beijing BioDee Biotechnology Co., Ltd.) by multiple cloning sites to obtain a gene silencing vector of pDE1005: proUBI: V-ATPase subunit E, a gene silencing vector of pDE1005: proUBI: COO2, and a gene silencing vector of pDE1005: proUBI: V-ATPase subunit E+COO2. The genes were synthesized by Sangon Biotech Engineering (Shanghai) Co. Ltd. The schematic diagram of the construction of the RNAi vector containing the fusion gene fragment formed by the V-ATPase subunit E gene and the COO02 double gene is shown in FIGS. 1*a*, 1*b* and 1*c*.

In an optional embodiment, the pDE1005 vector contains a rice intron, where a maize ubiquitin-1 promoter is located in the upstream of the rice intron. The fusion sequence of the maize ubiquitin-1 promoter and the rice intron is shown in SEQ ID NO: 7. In the hairpin structures of the three constructed RNAi vectors, the forward gene sequences of the hairpin structures for constructing the three RNAi vectors are shown in SEQ ID NO: 4, SEQ ID NO: 5 and SEQ ID NO: 6, respectively, the intron sequence is shown in SEQ ID NO: 8, and the reverse-complementary sequences are reverse-complementary to the sequences of SEQ ID NO: 4, SEQ ID NO: 5 and SEQ ID NO: 6, respectively.

Embodiment 3 *Agrobacterium tumefaciens*-Mediated Transformation of Fielder Spring Wheat with RNAi Vectors of pDE1005: proUBI: V-ATPase Subunit E, pDE1005: proUBI: COO2, and pDE 1005: proUBI: V-ATPase Subunit E+COO2

1.1. Pre-Culture of Immature Embryos

Immature seeds at 13-14 days after flowering and pollination (1.0-1.2 mm in size of immature embryo) were sterilized with 70% alcohol for 1-2 minutes and 15% sodium hypochlorite for 15 minutes, and washed with sterile water for 4-5 times.

1.2. Co-Culture of *Agrobacterium* and Immature Embryogenic Callus

At room temperature, the *Agrobacterium* cells were collected by centrifugation at 3500 rpm for 10 minutes and removing the supernatant, and then resuspended with 1/10 WCC resuspending solution (i.e., MS basic medium) in a ratio of 1:2. The wheat immature embryos were transferred to the *Agrobacterium* solution for 30 minutes of infection, and then the callus was transferred onto a sterile filter paper in a sterilized Petri dish, and co-cultured for 2 days (immature embryos) under dark conditions at 25° C.

The immature embryogenic calli after being co-cultured for 2 days were transferred to IESX1 selection medium (MS basic medium (containing MS vitamins)+30 g $L^{-1}$ of sucrose+2.0 mg $L^{-1}$ of dicamba+250 mg $L^{-1}$ of carbenicillin (Cb)+5 mg $L^{-1}$ of phosphinothricin (PPT), and pH 5.8) and cultured under dark conditions at 25° C. for 2 weeks, then transferred to IESX2 selection medium (MS basic medium (containing MS vitamins)+30 g $L^{-1}$ of sucrose+2.0 mg $L^{-1}$ of dicamba+250 mg $L^{-1}$ of carbenicillin (Cb)+10 mg $L^{-1}$ of phosphinothricin (PPT), and pH 5.8) and cultured under dark conditions at 25° C. for 2-3 weeks.

1.3. Screening of Resistant Regenerated Plants

The screened immature embryogenic calli were transferred to IEFH medium (MS basic medium (containing MS vitamins)+20 g $L^{-1}$ of sucrose+0.2 mg $L^{-1}$ of 2,4-Dichlorophenoxyacetic acid (2,4-D)+250 mg $L^{-1}$ of Cb+5 mg $L^{-1}$ of PPT, and pH=5.8) and cultured at 25° C. for 3-4 weeks under light. The MS vitamins were purchased from Sigma.

The screened mature embryogenic calli were transferred to XCFH differentiation medium (MS basic medium (without MS vitamins)+20 g $L^{-1}$ of sucrose+10.0 mg $L^{-1}$ of B1 vitamin+1.0 mg $L^{-1}$ of B3 vitamin+1.0 mg $L^{-1}$ of B6 vitamin+2.0 mg $L^{-1}$ of glycine+5.0 mg $L^{-1}$ of Glutamine+ 0.2 mg $L^{-1}$ of indoleacetic acid (IAA)+250 mg $L^{-1}$ of Cb+5 mg $L^{-1}$ of PPT, and pH 5.8) and cultured at 25° C. for 3-4 weeks to differentiate plants.

The seedlings growing to 2-3 cm were transferred to a rooting culture medium (½MS medium (containing MS vitamins)+20 g $L^{-1}$ of sucrose+250 mg $L^{-1}$ of Cb+5 mg $L^{-1}$ of PPT, and pH 5.8), and cultured at 25° C. under light for 3-4 weeks. Then, the robust, resistant plants were transplanted into flower pots.

Among them, the *Agrobacterium* used was *Agrobacterium* EHA105. The composition of MS basic medium included: 4.4 g/L of MS, 30 g/L of sucrose, and pH 5.8, and the MS medium is purchased from Sigma company.

PCR Detection of Transgenic Wheat

Positively identified PCR primers (PDE1005-FP: ATGACAGTTCCACGGCAGTAGATA (SEQ ID NO: 9) and intron-RP: TTTCTTGGTTAGGACCCTTTTCTCTT (SEQ ID NO: 10)) were used to detect the target gene. The results showed that specific DNA fragments were amplified by the designed PCR-specific primers. However, when using non-transformed wheat genomic DNA as a template, no fragments were amplified.

In this embodiment, the plant expression vector was transformed into *Agrobacterium tumefaciens*, and the *Agrobacterium tumefaciens* strains respectively containing V-ATPase subunit E, COO2 and V-ATPase subunit E+COO2 gene plant overexpression vectors were obtained for transforming wheat. The constructed *Agrobacterium tumefaciens* strains were used to transform wheat immature embryos to obtain the transgenic wheat plants detected by PCR.

Among them, the *Agrobacterium tumefaciens* used was *Agrobacterium tumefaciens* EHA105, and the competent cells were purchased from Shanghai Wedi Biotechnology Co., Ltd.

Embodiment 4 Identification of TI Generation Wheat Plants with RNAi Vectors of pDE1005: proUBI: V-ATPase Subunit E, pDE1005: proUBI: COO2, and pDE1005: proUBI: V-ATPase Subunit E+COO2 in Aphid Resistance Wheat aphids of the same age were inoculated on the tender leaves of the transgenic plants to be detected and three wild-type wheat. Each plant was inoculated with 10 aphids. After 10 days of cultivation, the number of aphids on the leaves was counted. The results were shown in Tables 1-3. Compared with the wild-type control, the TI generation wheat plants with RNAi vectors of pDE1005: proUBI: V-ATPase subunit E, pDE1005: proUBI: COO2, and pDE1005: proUBI: V-ATPase subunit E+COO2 obtained were significantly improved in aphid resistance.

By comparing the insect-resistant effects of T1 generation wheat plants with RNAi vectors of pDE1005: proUBI: V-ATPase subunit E, pDE1005: proUBI: COO2, and pDE1005: proUBI: V-ATPase subunit E+COO2, the transgenic wheat plants with pDE1005: proUBI: V-ATPase subunit E+COO2 had the best insect-resistant effect.

TABLE 1

Identification of transgenic wheat plants with pDE1005: proUBI: V-ATPase subunit E in aphid resistance

| Material | Total number of aphids per plant | Average value | Significant difference analysis (p-value) |
|---|---|---|---|
| CK1 | 246 | 244 | |
| CK2 | 212 | | |
| CK3 | 274 | | |
| V1-1 | 43 | 47 | 0.007373 |
| V1-4 | 47 | | |
| V1-7 | 51 | | |
| V2-1 | 62 | 67.7 | 0.0122738 |
| V2-2 | 73 | | |
| V2-4 | 68 | | |
| V3-3 | 55 | 54.7 | 0.0060112 |
| V3-4 | 49 | | |
| V3-5 | 60 | | |
| V4-2 | 39 | 36.3 | 0.008315 |
| V4-5 | 37 | | |
| V4-7 | 33 | | |
| V5-1 | 52 | 50 | 0.007877 |
| V5-2 | 48 | | |
| V5-3 | 50 | | |

TABLE 2

Identification of transgenic wheat plants with pDE1005: proUBI: COO2 in aphid resistance

| Material | Total number of aphids per plant | Average value | Significant difference analysis (p-value) |
|---|---|---|---|
| CK1 | 246 | 244 | |
| CK2 | 212 | | |
| CK3 | 274 | | |
| C1-3 | 77 | 75 | 0.0077974 |
| C1-4 | 69 | | |
| C1-7 | 79 | | |
| C2-2 | 60 | 58.7 | 0.0086244 |
| C2-5 | 57 | | |
| C2-7 | 59 | | |
| C3-3 | 66 | 68.3 | 0.0076491 |
| C3-4 | 65 | | |
| C3-5 | 74 | | |
| C4-1 | 70 | 66 | 0.0106326 |
| C4-3 | 65 | | |
| C4-4 | 63 | | |
| C5-1 | 55 | 54.7 | 0.0064858 |
| C5-5 | 50 | | |
| C5-7 | 59 | | |

TABLE 3

Identification of transgenic wheat plants with pDE1005: proUBI: V-ATPase subunit E + COO2 in aphid resistance

| Material | Total number of aphids per plant | Average value | Significant difference analysis (p-value) |
|---|---|---|---|
| CK1 | 246 | 244 | |
| CK2 | 212 | | |
| CK3 | 274 | | |
| VC1-1 | 14 | 14 | 0.0072 |
| VC1-3 | 17 | | |
| VC1-6 | 11 | | |
| VC2-2 | 0 | 1 | 0.0056 |
| VC2-3 | 2 | | |
| VC2-6 | 1 | | |
| VC3-2 | 17 | 20 | 0.0059 |
| VC3-4 | 20 | | |
| VC3-6 | 23 | | |
| VC4-1 | 9 | 12 | 0.0070 |
| VC4-3 | 16 | | |
| VC4-4 | 11 | | |
| VC5-3 | 21 | 26.7 | 0.0056 |
| VC5-5 | 26 | | |
| VC5-8 | 33 | | |

The results showed that the five TI generation wheat plants with the RNAi vector of pDE1005: proUBI: V-ATPase subunit E+COO2 had significantly lower number of aphids than that of the wild-type control, and had better anti-insect effect than those of the TI generation wheat plants with RNAi vectors of pDE1005: proUBI: V-ATPase subunit E and pDE1005: proUBI: COO2.

The above-mentioned specific implementation can be partially adjusted by those skilled in the art in different ways without departing from the principle and purpose of the present invention. The protective scope of the present invention is subject to the claims and is not limited by the above specific implementation, and each implementation within the protective scope of the present invention is bound by the present invention.

What is claimed is:

1. A recombinant nucleotide sequence, wherein the nucleotide sequence is shown in SEQ ID NO. 6.

2. A double-stranded RNA, wherein the sense strand of said dsRNA is encoded by the nucleotide sequence according to claim 1, and wherein the presence of the double-stranded RNA in a plant enhances a resistance of the plant to pests.

3. A method of enhancing resistance of a plant to pests, the method comprising:
   1) constructing a recombinant expression vector that expresses the double-stranded RNA of claim 2;
   2) transforming the recombinant expression vector into *Agrobacterium* to obtain a transformed *Agrobacterium*, and infecting an immature embryo of the plant with the transformed *Agrobacterium* to obtain immature embryogenic calli; and
   3) screening the immature embryogenic calli with an antibiotic to obtain a seedling comprising said recombinant expression vector providing enhanced resistance.

4. The method according to claim 3, wherein the pests are aphids.

5. The method according to claim 3, wherein the plant is selected from the group consisting of *Arabidopsis*, rice, wheat, corn, cotton, soybean, rape, *sorghum*, tobacco, *chrysanthemum*, Chinese cabbage, cabbage, radish, and tomato.

6. The method according to claim 3, wherein the plant is wheat, the recombinant expression vector is a silencing RNAi vector, wherein the RNAi vector is constructed with a maize ubiquitin-1 promoter to drive expression of the double-stranded RNA, and the maize ubiquitin-1 promoter is a constitutive promoter, and wherein the step of infecting the immature embryo comprises: transferring the immature embryo of the wheat plant to a transformed *Agrobacterium* solution to obtain the infected immature embryo, incubating the infected immature embryo on a culture medium under dark conditions to obtain the immature embryogenic calk, and performing a screening on resistant regenerated plants of the immature embryogenic calli to obtain resistant wheat seedlings.

* * * * *